US006768782B1

(12) United States Patent
Hsieh et al.

(10) Patent No.: US 6,768,782 B1
(45) Date of Patent: Jul. 27, 2004

(54) ITERATIVE METHOD FOR REGION-OF-INTEREST RECONSTRUCTION

(75) Inventors: Jiang Hsieh, Brookfield, WI (US); Jean-Baptiste Thibault, Milwaukee, WI (US); Charles A. Bouman, West Lafayette, IN (US); Ken Sauer, South Bend, IN (US)

(73) Assignees: University of Notre Dame du Lac, Notre Dame, IN (US); Purdue University, West Lafayette, IN (US); GE Medical Systems Global Technology Company, LLC, Waukesha, WI (US)

( * ) Notice: Subject to any disclaimer, the term of this patent is extended or adjusted under 35 U.S.C. 154(b) by 74 days.

(21) Appl. No.: 10/319,689

(22) Filed: Dec. 16, 2002

(51) Int. Cl.[7] ............................................... A61B 6/03
(52) U.S. Cl. ............................... 378/8; 378/4; 378/901
(58) Field of Search .......................... 378/4, 8, 15, 19, 378/901

(56) References Cited

U.S. PATENT DOCUMENTS 4,878,169 A * 10/1989 Toner et al. ................ 382/131

OTHER PUBLICATIONS

Allain et al., "Approche regularisee en reconstruction tomographique 3D helicoidale," *Proceedings of the 2001 GRETSI Symposium on Signal and Image Processing*, 2001, Toulouse, France (An English abstract is printed on the front page of the reference).

Bouman et al., "Multiple Resolution Segmentation of Textured Images" *IEEE Transactions on Pattern Analysis and Machine Intelligence* vol. 13, No. 2, Feb. 1991.
Bouman et al., "A Local Update Strategy for Iterative Reconstruction from Projections" *IEEE Transactions on Signal Processing* vol. 41, No. 2, Feb. 1993.
Bouman et al., "A Unified Approach to Statistical Tomography Using Coordinate Descent Optimization" *IEEE Transactions on Image Processing* vol. 5, No. 3, Mar. 1996.
Delaney et al., "Multiresolution Tomographic Reconstruction Using Wavelets" *IEEE Transactions on Image Processing* vol. 4, No. 6, Jun. 1995.
Dempster et al., "Maximum Likelihood from Incomplete Data via the EM Algorithm" *Howard University and Educational Testing Service*. [Read before the Royal Statistical Society at a meeting organized by the Research Section on Dec. 8th, 1976,].

(List continued on next page.)

*Primary Examiner*—David V. Bruce
(74) *Attorney, Agent, or Firm*—Jagtiani + Guttag (57) ABSTRACT

An imaging system is provided including a source generating an x-ray beam and a detector array receiving the x-ray beam and generating projection data corresponding to at least a scanned portion of an object. An image reconstructor is electrically coupled to said detector array and reconstructs an image of the scanned portion of the object for a full field-of-view in response to said projection data using a dual iterative reconstruction technique. The dual iterative reconstruction technique includes reconstructing the full field-of-view using a first resolution and reconstructing a region-of-interest within the full FOV using a second resolution. A method is also provided for reconstructing an image using projection data from such an imaging system.

27 Claims, 3 Drawing Sheets

OTHER PUBLICATIONS

Derin et al., "Modeling and Segmentation of Noisy and Textured Images Using Gibbs Random Fields" *IEEE Transactions on Pattern Analysis and Machine Intelligence* vol. PAMI–9, No. 1, Jan. 1987.

Hudson et al., "Accelerated Image Reconstruction Using Ordered Subsets of Projection Data" *IEEE Transactions on Medical Imaging* vol. 13, No. 4, Dec. 1994.

Herbert et al., "A Generalized EM Algorithm for 3–D Bayesian Reconstruction From Poisson Data Using Gibbs Priors" *IEEE Transactions on Medical Imaging* vol. 8, No. 2, Jun. 1989.

Kak et al., "Algebraic Reconstruction Algorithms" *Principles of Computerized Tomographic Imaging* (IEEE Press, 1988), pp. 275–296 Note: *Principles of Computerized Tomographic Imaging* is now published by the Society for Industrial and Applied Mathmatics.

Lange et al., "EM Reconstruction Algorithms for Emission and Transmission Tomography" *Journal of Computer Assisted Tomography* vol. 8, No. 2, 1984.

Sahiner et al., "Region–of–Interest Tomography Using Exponential Radial Sampling" *IEEE Transactions on Image Processing* vol. 4, No. 8, Aug. 1995.

Shepp et al., "Maximum Likelihood Reconstruction for Emission Topography" *IEEE Transactions on Medical Imaging* vol. MI–1, No. 2, Oct. 1982.

* cited by examiner

ITERATIVE METHOD FOR REGION-OF-INTEREST RECONSTRUCTION

CROSS-REFERENCE TO RELATED APPLICATIONS

The present invention is related to U.S. patent application Ser. No. 10/319,674 entitled "Iterative Reconstruction Methods for Multi-Slice Computed Tomography" filed simultaneously herewith and the entire contents and disclosure of the above-identified application is hereby incorporated by reference.

BACKGROUND OF THE INVENTION

1. Field of the Invention

The present invention relates generally to multi-slice computed tomography (CT) imaging systems, and more particularly, to an apparatus and methods of reconstructing an image of an object for an imaging system.

2. Description of the Prior Art

A computed tomography (CT) imaging system typically includes an x-ray source that projects a fan-shaped x-ray beam through an object being imaged, such as a patient, to an array of radiation detectors. The beam is collimated to lie within an X-Y plane, generally referred to as an "imaging plane". Intensity of radiation from the beam received at the detector array is dependent upon attenuation of the x-ray beam by the object. Attenuation measurements from each detector are acquired separately to produce a transmission profile.

The x-ray source and the detector array are rotated within a gantry and around the object to be imaged so that a projection angle at which the x-ray beam intersects the object constantly changes. A group of x-ray attenuation measurements, i.e., integral projection data, from the detector array at one gantry angle is referred to as a "view". A "scan" of the object comprises a set of views made at different projection angles.

In an axial scan, the projection data is processed to construct an image that corresponds to a two-dimensional slice taken through the object. For discrete slices, iterative reconstruction of a full field of view may be performed in order to increase image quality. Multiple iterations are performed to approximately match a resulting reconstructed image to the acquired projection data.

Conventional methods for tomographic image reconstruction in single planes from axial mode data may be found in Avinash C. Kak and Malcolm Slaney, "Principles of Computerized Tomographic Imaging," Classics in Applied Mathematics, 33, SIAM, 2001, ISBN:089871494X, the entire contents and disclosure of which is hereby incorporated by reference, having been applied especially to X-ray CT since the 1970's. One of the earliest iterative methods for reconstruction, algebraic reconstruction technique (ART), is also discussed in Avinash C. Kak and Malcolm Slaney, "Principles of Computerized Tomographic Imaging," Classics in Applied Mathematics, 33, SIAM, 2001, ISBN:089871494X, the entire contents and disclosure of which is hereby incorporated by reference. References such as A. Delaney and Y. Bresler, "Multiresolution Tomographic Reconstruction Using Wavelets," IEEE Transactions on Image Processing, vol. 4 no. 6, pp. 799–813, June 1995, and B. Sahiner and A. Yagle, "Region-of-Interest Tomography Using Exponential Radial Sampling," IEEE Transactions on Image Processing, vol. 4 no. 8, pp. 1120–1127, August 1995, the entire contents and disclosures of which are hereby incorporated by reference, use non-iterative reconstruction methods based on alternative signal representations. In references A. Dempster, N. Laird and D. Rubin, "Maximum Likelihood from Incomplete Data via the EM Algorithm," Journal of the Royal Statistical Society B, vol. 1 no. 39, pp. 1–38, 1977, L. Shepp and Y. Vardi, "Maximum Likelihood Reconstruction for Emission Tomography," IEEE Transactions on Medical Imaging, vol. MI-1, no. 2, pp. 113–122, October 1982, and K. Lange and R. Carson, "EM Reconstruction Algorithms for Emission and Transmission Tomography," Journal of Computer Assisted Tomography, vol. 8 no. 2, pp. 306–316, April 1984, the entire contents and disclosures of which are hereby incorporated by reference, the "expectation-maximization" (EM) technique appears, in the general form, applied to emission tomography, and studied for both emission and transmission (such as X-ray CT). "Ordered subsets" methods for EM are presented in Hudson and Larkin, "Accelerated Image Reconstruction Using Ordered Subsets of Projection Data," IEEE Transactions on Medical Imaging, vol. 13 no. 4, pp. 601–609, December 1994, the entire contents and disclosure of which is hereby incorporated by reference. The Bayesian methods of T. Hebert and R. Leahy, "A Generalized EM Algorithm for 3-D Bayesian Reconstruction from Poisson data Using Gibbs Priors," IEEE Transactions on Medical Imaging, vol. 8 no. 2, pp. 194–202, June 1989, the entire contents and disclosure of which is hereby incorporated by reference, are an example of "maximum a posteriori" (MAP) techniques, and K. Sauer and C. A. Bouman, "A Local Update Strategy for Iterative Reconstruction from Projections," IEEE Transactions on Signal Processing, vol. 41, no. 2, pp. 534–548, February 1993, and C. A. Bouman and K. Sauer, "A Unified Approach to Statistical Tomography Using Coordinate Descent Optimization," EEE Transactions on Image Processing, vol. 5, no. 3, pp. 480–492, March 1996, the entire contents and disclosures of which are hereby incorporated by reference, include MAP techniques with pixel updates. "Segmentation" of images is an imaging process, examples of which are found in H. Derin and H. Elliot, "Modeling and Segmentation of Noisy and Textured Images Using Gibbs Random Fields," IEEE Transactions on Pattern Analysis and Machine Intelligence, vol. PAMI-9, pp. 39–55, January 1987, and C. Bouman and B. Liu, "Multiple Resolution Segmentation of Textured Images," IEEE Transactions on Pattern Analysis and Machine Intelligence, vol. PAMI-13, no. 2, pp. 99–113, February 1991, the entire contents and disclosures of which are hereby incorporated by reference, and other references cited therein.

To reduce the total scan time required for multiple slices, a "helical" scan may be performed. Helical scan techniques allow for large volumes to be scanned at a quicker rate using a single x-ray source. To perform a "helical" scan, the patient is moved along a z-axis synchronously with the rotation of the gantry, while data for a prescribed number of slices are acquired. Such a system generates a single helix from a fan beam or cone beam helical scan. The helix mapped out by the fan beam or cone beam yields projection data from which images in each prescribed slice may be reconstructed. In addition to reducing scan time, helical scanning provides other advantages such as better use of injected contrast, improved image reconstruction at arbitrary locations, and better three-dimensional images.

In order to reconstruct the image, typically, a filtered backprojection (FBP) reconstruction approach is utilized. In FBP the projection data is filtered before being backprojected onto an image matrix. The filtering mathematically reverses image blurring, restoring the image to an accurate representation of the scanned object. Although FBP provides relatively quick image reconstruction, many approximations occur due to the imaging system's accounting for geometries and defects in a single iteration, resulting in an image containing blurring and artifacts.

In CT imaging a targeted reconstruction approach is a popular technique for improvement of image quality and spatial resolution. The targeted reconstruction technique involves using a higher resolution for a reconstruction field of view (RFOV) by reconstructing only the targeted area rather than the entire FOV. Since the image matrix size is typically limited, sampling density within the RFOV can be significantly improved by limiting size of the RFOV. The targeted reconstruction technique ensures that spatial resolution of the reconstructed image is limited by scanning hardware capabilities and not by matrix size of the image. 1For example, when the RFOV is 50 cm by 50 cm each image pixel is approximately 1 mm by 1 mm in size, versus 0.2 mm by 0.2 mm in size when the RFOV is 10 cm by 10 cm. For the RFOV of 50 cm by 50 cm, based on Nyquist sampling theory, the maximum supported spatial resolution is 5 line pairs (LP) per centimeter and for the RFOV of 10 cm by 10 cm the maximum supported spatial resolution is 25 LP/cm.

For filtered backprojection (FBP), targeted reconstruction is nearly identical to full FOV reconstruction. Projection data is weighted and filtered in a fashion similar to full FOV reconstruction. During backprojection, only the scanned area corresponding to the RFOV is utilized from the projection data. Reconstruction is not performed on remaining scanned area outside the RFOV.

Unfortunately, targeted reconstruction is not applicable to iterative reconstruction for either discrete slices or for continuous multi-slice scanning. In iterative reconstruction, forward projection samples based on the reconstructed image need to be compared with the acquired or measured projections. The difference between the forward projection samples and the measured projections are used as a basis for updating the reconstructed image.

When the reconstructed image represents a small portion of the scanned object, the forward projections are an underestimation of measured projections. Consequently, inherent bias is designed into the iterative reconstruction and the imaging system is not able to match the projection data in a manner which reconstructs an image that accurately represents the actual scanned object. Thus, information of the object outside a region-of-interest is lacking in current systems, which negatively effects estimated projections.

One reason that filtered backprojection is commonly used over iterative reconstruction is its speed. With ever increasing computational speed of computers and a desire for improved image quality is a need for and feasibility of iterative reconstruction.

It would therefore be desirable to provide a method of iterative image reconstruction that minimizes noise and artifacts in both single slice and multi-slice CT imaging systems, and at the same time maintains or increases image quality for a targeted region-of-interest.

SUMMARY OF THE INVENTION

The present invention provides an apparatus and methods for reconstructing an image of an object for an imaging system. An imaging system is provided, including a source generating an x-ray beam and a detector array receiving the x-ray beam and generating projection data corresponding to at least a scanned portion of an object. An image reconstructor is electrically coupled to the detector array and reconstructs an image of the scanned portion of the object for a full field-of-view in response to the projection data using a dual iterative reconstruction technique. The dual iterative reconstruction technique includes reconstructing the full field-of-view using a first resolution and reconstructing a region-of-interest within the full FOV using a second resolution. A method is also provided for performing the same.

One of several advantages of the present invention is that it provides a reconstructed image for a full FOV having standard or lower resolution and, via iterative reconstruction, higher resolution for a region-of-interest within the full FOV. Thus, computation is reduced for areas outside the region-of-interest.

Another advantage of the present invention is that it accounts for areas outside the region-of-interest to increase accuracy of projection estimation and decrease time of convergence during iterative reconstruction.

Furthermore, the present invention provides a reconstructed image of improved quality, especially in a region-of-interest, which for diagnostic examination purposes is of higher importance.

Moreover, the present invention provides multiple dual iterative reconstruction techniques and is thus versatile in application, since one dual iterative reconstruction technique may be better for one application over another.

According to a first broad aspect of the present invention, there is provided a imaging system comprising: a source generating a x-ray beam; a detector array receiving the x-ray beam and generating projection data corresponding to at least a scanned portion of an object based on the received x-ray beam; and an image reconstructor electrically coupled to the detector array for reconstructing an image of the scanned portion of the object for a full field-of-view in response to the projection data using a dual iterative reconstruction technique comprising: reconstructing the full field-of-view using a first resolution; and reconstructing a region-of-interest within the full field-of-view using a second resolution.

According to second broad aspect of the invention, there is provided a method of reconstructing an image of an object for an imaging system comprising: providing projection data corresponding to at least a scanned portion of an object; and reconstructing an image of the scanned portion of the object for a full field-of-view based on the projection data using a dual iterative reconstruction technique comprising: reconstructing the full field-of-view using a first resolution; and reconstructing a region-of-interest within the full field-of-view using a second resolution.

Other objects and features of the present invention will be apparent from the following detailed description of the preferred embodiment.

BRIEF DESCRIPTION OF THE DRAWINGS

The invention will be described in conjunction with the accompanying drawings, in which.

DETAILED DESCRIPTION OF THE PREFERRED EMBODIMENT

It is advantageous to define several terms before describing the invention. It should be appreciated that the following definitions are used throughout this application.

Definitions

Where the definition of terms departs from the commonly used meaning of the term, applicant intends to utilize the definitions provided below, unless specifically indicated.

For the purposes of the present invention, the term "forward model" refers to a description of the transformation from the image space of a scanned object to the projection space for a scanned object, as modeled after the operation of the CT imaging system. The operation of the forward model on an image vector is referred to as "forward projection."

For the purposes of the present invention, the term "maximum a-posteriori technique" refers to any of the image reconstruction techniques known in the art which measure the optimality of an image by a cost function including both a term measuring the match of the forward projected image to the measured data, and a term penalizing departure of the image from expected behavior. Such techniques are discussed in T. Hebert and R. Leahy, "A Generalized EM Algorithm for 3-D Bayesian Reconstruction from Poisson data Using Gibbs Priors," IEEE Transactions on Medical Imaging, vol. 8 no. 2, pp. 194–202, June 1989, K. Sauer and C. A. Bouman, "A Local Update Strategy for Iterative Reconstruction from Projections," IEEE Transactions on Signal Processing, vol. 41, no. 2, pp. 534–548, February 1993, and C. A. Bouman and K. Sauer, "A Unified Approach to Statistical Tomography Using Coordinate Descent Optimization," IEEE Transactions on Image Processing, vol. 5, no. 3, pp. 480–492, March 1996, the entire contents and disclosures of which are hereby incorporated by reference.

For the purposes of the present invention, the term "expectation-maximization technique" refers to a numerical method, elucidated in A. Dempster, N. Laird and D. Rubin, "Maximum Likelihood from Incomplete Data via the EM Algorithm," Journal of the Royal Statistical Society B, vol. 1 no. 39, pp. 1–38, 1977, L. Shepp and Y. Vardi, "Maximum Likelihood Reconstruction for Emission Tomography," IEEE Transactions on Medical Imaging, vol. MI-1, no. 2, pp. 113–122, October 1982, K. Lange and R. Carson, "EM Reconstruction Algorithms for Emission and Transmission Tomography," Journal of Computer Assisted Tomography, vol. 8 no. 2, pp. 306–316, April 1984, and T. Hebert and R. Leahy, "A Generalized EM Algorithm for 3-D Bayesian Reconstruction from Poisson data Using Gibbs Priors," IEEE Transactions on Medical Imaging, vol. 8 no. 2, pp. 194–202, June 1989, the entire contents and disclosures of which are hereby incorporated by reference, of achieving a maximum-likelihood (ML) or maximum a posteriori (MAP) estimate. Expectation-maximization techniques, at each iteration, operate on an approximation of the cost function to be optimized, with that approximation based on the current state of the estimate and on the observed data.

For the purposes of the present invention, the term "ordered subsets" refers to a technique, an example of which is presented in Hudson and Larkin, "Accelerated Image Reconstruction Using Ordered Subsets of Projection Data," IEEE Transactions on Medical Imaging, vol. 13 no. 4, pp. 601–609, December 1994, the entire contents and disclosure of which is hereby incorporated by reference, of operating on a sequence of subsets of observed data in estimating an image vector.

For the purposes of the present invention, the term "interest level criteria associated with each pixel" refers to a metric of significance attached to each image pixel, representing the pixel's relative importance to visual interpretation of the image content.

For the purposes of the present invention, the term "pixel updates" refers to the adjustments of the values in an image vector during iterative reconstruction, in response to projection data and the current state of the image vector.

Description

While the present invention is described with respect to apparatus and methods reconstructing an image of an object for a multi-slice CT imaging system, the following apparatus and method is capable of being adapted for various purposes and is not limited to the following applications: magnetic resonance imaging (MRI) systems, CT systems, radiotherapy systems, X-ray imaging systems, ultrasound systems, nuclear imaging systems, magnetic resonance spectroscopy systems, and other applications known in the art.

Figure 3:
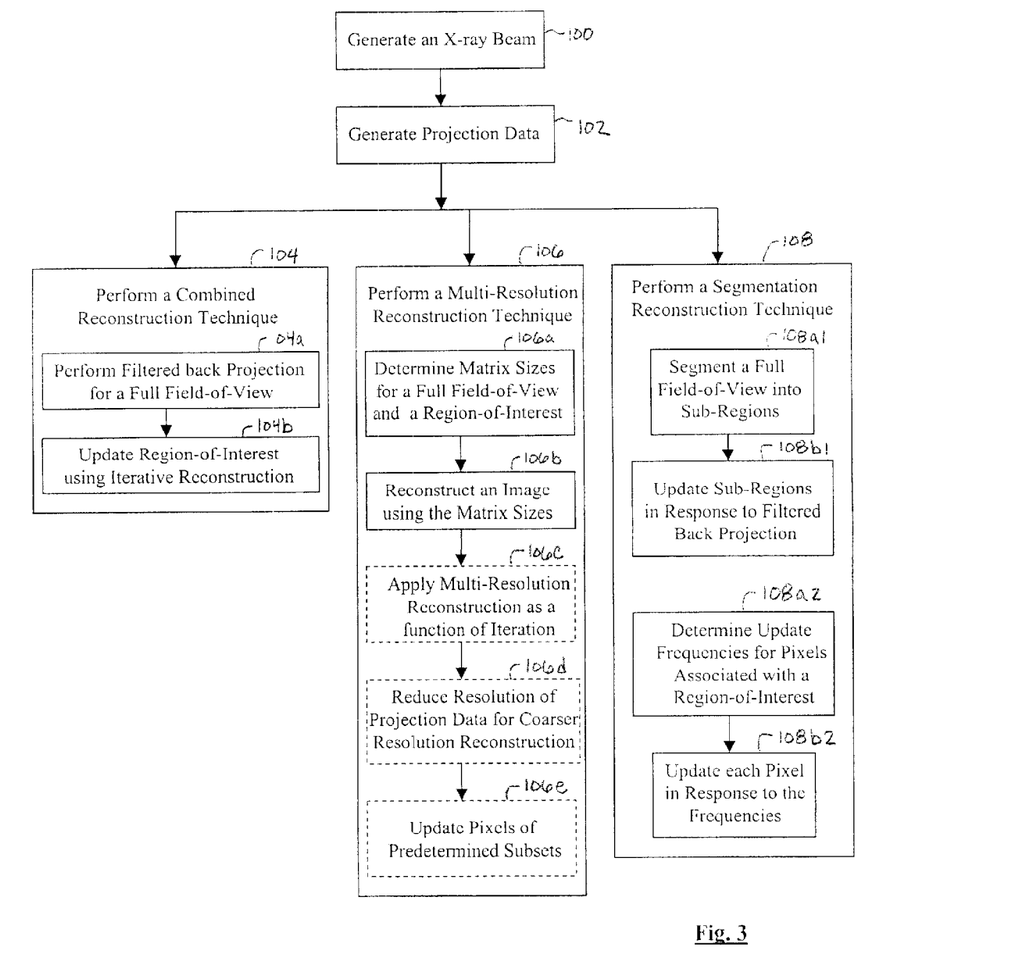
FIG. 3 is a logic flow diagram illustrating methods of reconstructing an image in accordance with multiple embodiments of the present invention.

Also, in the following description the terms "dual iterative reconstruction technique" includes reconstructing a full field-of-view (FOV) using a first resolution and reconstructing a region-of-interest within the full FOV using a second resolution. Resolution may refer to different sampling rates, various levels of detail or sharpness, quality of reconstruction, or other resolution interpretations known in the art. In the following description, FIG. 3 illustrates several different embodiments of the present invention of a dual iterative reconstruction technique. The illustrative embodiments are not meant to be all-inclusive, but are for example purposes only. A dual iterative reconstruction technique may be performed using various methods known in the art, including methods illustrated in the following description, individually or in combination thereof.

Additionally, in the following description the term "plane" may refer to a conventional two-dimensional geometric plane or may also refer to a three-dimensional surface or object having varying thickness or depth.

In the following description, various operating parameters and components are described for one constructed embodiment. These specific parameters and components are included as examples and are not meant to be limiting.

Figure 1:
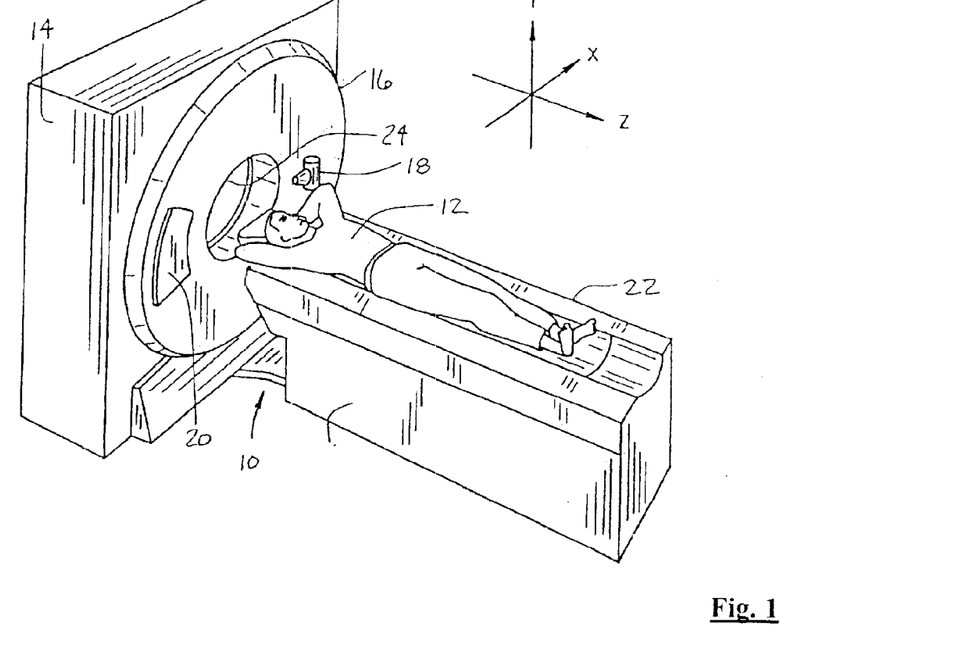
FIG. 1 is a pictorial view of a multi-slice CT imaging system utilizing a method of reconstructing an image in accordance with an embodiment of the present invention.

Referring now to FIG. 1, a pictorial view of a multi-slice CT imaging system 10, utilizing a method of reconstructing an image of a medical patient 12 in accordance with a preferred embodiment of the present invention is shown. An imaging system 10 includes a gantry 14 that has a rotating inner portion 16 containing a x-ray source 18 and a detector array 20. X-ray source 18 projects a beam of x-rays (not shown in FIG. 1) towards detector array 20. X-ray source 18 and detector array 20 rotate about an operably translatable table 22. Translatable table 22 is translated along a z-axis between x-ray source 18 and detector array 20 to perform either an axial scan or a helical scan. The beam of x-rays, after passing through medical patient 12, within a patient bore 24, is detected at detector array 20 to generate projection data (not shown) that is used to create a CT image.

Figure 2:
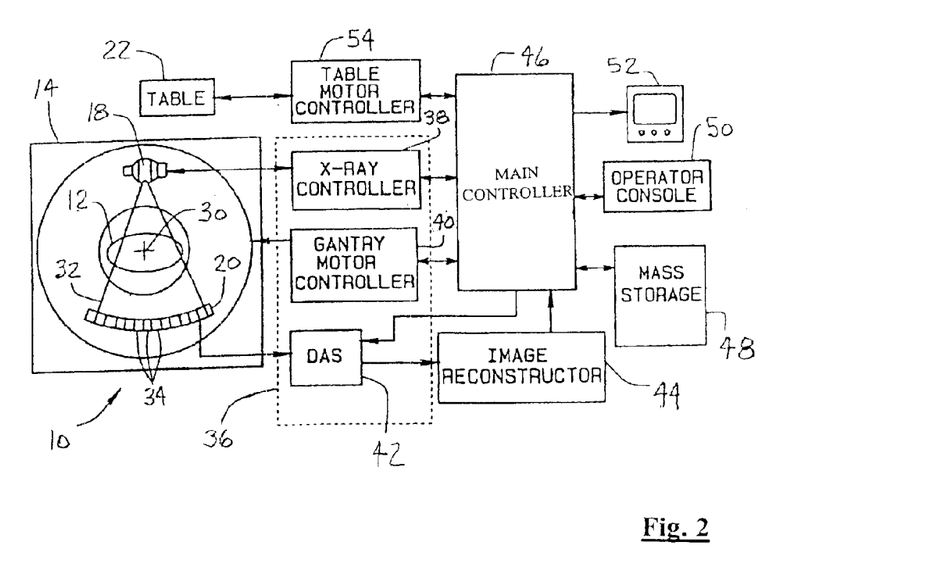
FIG. 2 is a block diagrammatic view of the multi-slice CT imaging system in accordance with an embodiment of the present invention.

Referring now to FIG. 2, a block diagrammatic view of system 10 of FIG. 1 is shown. Source 18 and detector array 20 rotate about a center axis 30. Beam of x-rays 32 is received by multiple detector elements 34 in multiple detector rows. Each detector element 34 generates an electrical signal corresponding to the intensity of an impinging x-ray beam, such as beam 32. As beam 32 passes through patient 12, beam 32 is attenuated. Rotation of inner portion 16 of gantry 14 and the operation of source 18 are governed by a control mechanism 36. Control mechanism 36 includes an x-ray controller 38 that provides power and timing signals to source 18 and a gantry motor controller 40 that controls the rotational speed and position of inner portion 16. A data acquisition system (DAS) 42 samples analog data from the detector elements 34 and converts the analog data to digital signals for subsequent processing. An image reconstructor 44 receives sampled and digitized x-ray data from the DAS 42 and performs high-speed image reconstruction. A main controller 46 stores the CT image (not shown) in a mass storage device 48.

Main controller 46 also receives commands and scanning parameters from an operator via an operator console 50. A display 52 allows an operator (not shown) to observe the reconstructed image and other data from main controller 46. Operator supplied commands and parameters are used by the main controller 46 in operation of DAS 42, x-ray controller 38, and gantry motor controller 40. In addition, main controller 46 operates a table motor controller 54, which translates table 22 to position patient 12 in gantry 14.

X-ray controller 38, gantry motor controller 40, image reconstructor 44, main controller 46, and table motor controller 54 are preferably based on microprocessors such as a computer having a central processing unit, memory (RAM and/or ROM), and associated input and output buses. X-ray controller 38, gantry motor controller 40, image reconstructor 44, the main controller 46, and table motor controller 54 may be a portion of a central control unit or may each be stand-alone components as shown.

Referring now to FIG. 3, a logic flow diagram illustrating methods of reconstructing an image in accordance with multiple embodiments of the present invention is shown. For convenience, the method of reconstructing an image illustrated in FIGS. 3, 4, 5 and 6 will be described using the components of the system described in shown in FIGS. 1 and 2.

In step 100, source 18 generates x-ray beam 32, which is directed through an examining portion of the patient 12 towards detector array 20.

In step 102, the detector array 20 receives x-ray beam 32 and generates projection data corresponding to a scanned portion of patient 12.

Figure 4:
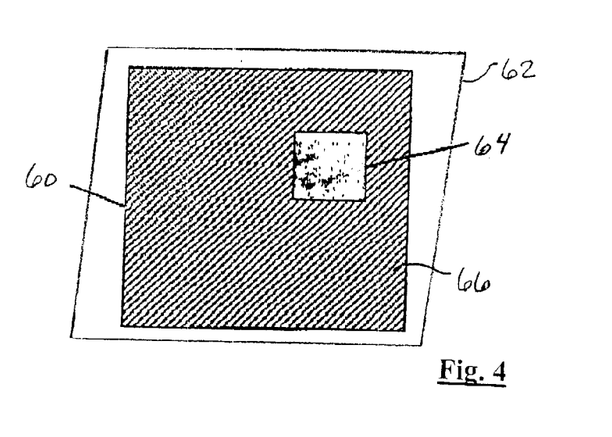
FIG. 4 is a two-dimensional view of a full field-of-view of a reconstruction plane in accordance with multiple embodiments of the present invention.

Referring now to FIGS. 3 and 4, in FIG. 4 an example two-dimensional view of a full FOV 60 of a reconstruction plane 62 is shown. A region-of-interest 64 exists within full FOV 60. The region-of-interest 64 is a first area within the full FOV 60 where special interest resides, such that, by performing the following steps quality of the reconstructed image is better for the region-of-interest 64 than for a second area 66 outside region-of-interest 64.

In steps 104, 106 and 108, an image of the scanned portion of the patient 12 is reconstructed for full FOV 60 in response to projection data using a dual iterative reconstruction technique. The dual iterative reconstruction technique may be selected from a combined reconstruction technique, a multi-resolution reconstruction technique, a segmentation reconstruction technique, or combination thereof. As stated above, other reconstructive techniques known in the art may be used in combination, or in combination with one of the above-described dual iterative reconstructive techniques to reconstruct the image.

In step 104, a combined reconstruction technique is illustrated.

In sub-step 104*a*, the image is reconstructed for full FOV 60 using filtered backprojection. As stated above in current iterative reconstruction, information pertaining to a patient that is outside region-of-interest 64, is lacking information that causes quality of generated estimated projections to be limited. In an embodiment of the present invention, the lacking information is provided by initially using filtered backprojection for full FOV 60.

In sub-step 104*b*, region-of-interest 64, within full FOV 60, is updated using iterative reconstruction. The iterative reconstruction is performed using a technique selected from at least one of a maximum a-posteriori technique, an expectation-maximization technique, an ordered subsets technique, or other technique known in the art. Although the second area 66 may not have similar noise suppression characteristics to those of the area within region-of-interest 64, the filtered backprojection provides adequate information for estimation of forward projections.

Progress of the iterative reconstruction may be continuously monitored, which may include updating the filtered backprojection image when a convergence measure does not satisfy a pre-determined condition with iterative reconstruction. When the convergence measure does not satisfy the pre-determined condition, the area reconstructed by filtered backprojection may be updated by iterative reconstruction to improve accuracy of the image. Computational complexity is reduced by completing iterative reconstruction for only region-of-interest 64 rather than full FOV 60.

In step 106, a multi-resolution reconstruction technique is illustrated. An underlying assumption exists for the multi-resolution reconstruction technique, which is that accuracy of second area 66 outside region-of-interest 64 may be coarser than accuracy of the area within region-of-interest 64. The multi-resolution reconstruction technique includes reconstructing an image with an improved spatial resolution for region-of-interest 64 than for second area 66.

Figure 5:
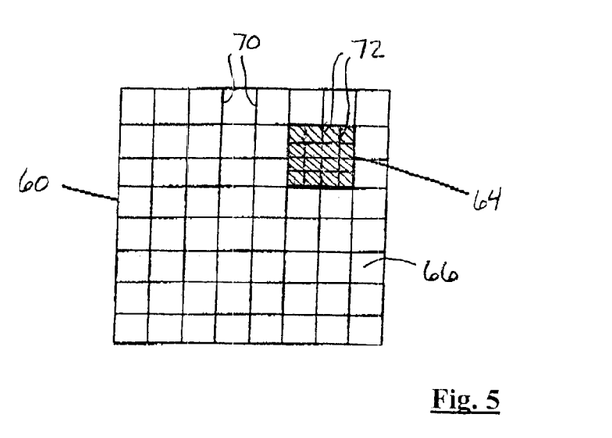
FIG. 5 is a two-dimensional view of the full field-of-view for a multi-resolution reconstruction technique in accordance with multiple embodiments of the present invention.

Referring now to FIGS. 3 and 5, in FIG. 5 a two-dimensional view of full FOV 60 for a multi-resolution reconstruction technique with an example overlaid first matrix 70 is shown. Full FOV 60 is divided into a first matrix 70 having a first resolution. A portion of first matrix 70 corresponding to region-of-interest 64 is further divided to have a second resolution greater than the first resolution, which is represented by a second matrix 72.

In sub-step 106*a*, the size of first matrix 70 is determined and the size of second matrix 72 is determined for region-of-interest 64. The resolution within region-of-interest 64 may be any integer factor larger than second area 66. As known in the art, an amount of computation scales roughly to a square of size of a resolution matrix corresponding to the image for filtered backprojection techniques, and roughly linearly for iterative methods. Thus, computation for second area 66 is reduced and computation for full FOV 60 is reduced. Of course, the more the size of first matrix 70 is reduced the less accurate the object estimation. So a balance is created between the size of first matrix 70 and reconstructed image quality. The sizes of matrices 70 and 72 may be determined by simulations, phantom experiments, and clinical testing.

In sub-step 106b, the image is reconstructed using the sizes of matrixes 70 and 72. Filtered backprojection, iterative reconstruction, other reconstruction techniques, or a combination thereof may be used.

The multi-resolution reconstruction technique may be applied for both in-plane sampling and orthogonally to multiple planes. Orthogonally to a plane refers to depth or thickness of the plane. A slice thickness may be larger for the area of a plane within region-of-interest 64 and smaller for second area 66, or vice versa.

In sub-step 106c, the multi-resolution reconstruction technique may be applied as a function of iteration. For example, resolution of an initial matrix may be coarser than a desired final matrix to quickly reach a convergence level for a particular matrix size. Resolution of the initial matrix may be increased iteratively, where each iteration has a corresponding reconstructed image, when certain criteria are met. When difference between an image produced by the current iteration and that produced by a previous iteration is smaller than a predetermined threshold, the criteria are met. Alternatively, when the difference between a forward projection of the current image and a measured projection is smaller than predetermined threshold, the criteria are met.

An estimation of the object, corresponding to a matrix that is larger than a previous matrix in an iterative sequence of matrices, may be an interpolated version of an image resulting from reconstruction, using the previous matrix. The interpolation used may be nearest neighbor, linear, high order, or other interpolation known in the art. In so doing, the image reconstructor 44 may vary the number of pixel updates for differing resolutions depending upon interest level associated with each pixel. By performing the aforementioned, initial estimation is accurate and therefore speed of convergence is increased.

In sub-step 106d, resolution of the projection data may also be reduced for coarser resolution reconstructions. Reduction in projection data resolution reduces computation for coarser resolution reconstruction with minor degradation in quality of image reconstruction.

In sub-step 106e, the projection data may be separated into pre-determined subsets. Pixels corresponding to the pre-determined subsets are then updated. Although sub-steps 106d and 106e are shown as separate sub-steps, they may be performed as part of sub-step 106c.

In step 108, methods for performing segmentation reconstruction techniques are illustrated. In conventional iterative reconstruction all pixels within a region-of-interest are updated either in a sequential, pseudo-random, or synchronized manner, which aids in convergence of a reconstruction process. By performing a segmentation reconstruction technique image reconstructor 44 performs the same number of iterations for approximately the entire region-of-interest 64. The segmentation reconstruction techniques update portions of region-of-interest 64 for areas that exhibit significant spatial variation more often than areas that are relatively flat.

Figure 6:
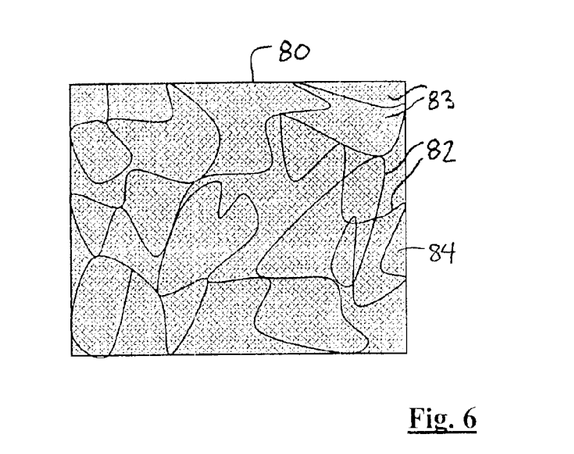
FIG. 6 is a two-dimensional view of a full field-of-view for a segmentation reconstruction technique in accordance with multiple embodiments of the present invention.

Referring now to FIGS. 3 and 6, in FIG. 6 an example cross-sectional view of a full FOV 80 for a segmentation reconstruction technique is shown. In sub-step 108a1, a segmentation reconstruction technique may include segmenting full FOV 80 into sub-regions 82. Sub-regions 82 and pixels 83 are updated in response to edge or gradient information. Edge information refers to visual discontinuities in an image and gradient information refers to change in density as a function of position along the x-axis, y-axis, or z-axis. A gradient vector is defined as:

$$\hat{G}=[d \text{ density}/dx, d \text{ density}/dy, d \text{ density}/dz] \quad (1)$$

Edges are generally detected as positions where magnitude of the gradient vector is large. For example, where $\|G\|$ is greater than a threshold T an edge is detected.

In sub-step 108b1, each of sub-regions 82 are updated in response to analysis of filtered backprojection data. Frequency of updating each sub-region 82 is monitored during filtered backprojection and sub-regions with an update frequency above a predetermined update frequency value continue to be updated, while sub-regions with an update frequency below the predetermined update frequency value are not updated or are updated with a lower frequency.

In sub-step 108a2, image reconstructor 44 determines frequency with which each pixel 83 in a plurality of pixels 84 associated with a region-of-interest 86 is updated during reconstruction iterations.

In sub-step 108b2, each pixel 83 is updated in response to the frequency, similarly to sub-regions 82 in sub-step 108b.

The above-described steps and sub-steps are meant to be an illustrative example, and the steps may be performed synchronously or in a different order, depending upon the application.

The present invention provides multiple methods for reconstructing an image using a dual iterative reconstruction technique that provides a reconstructed image for a full FOV, having higher image quality for a region-of-interest within the full FOV. The technique minimizes computation, accounts for areas outside the region-of-interest, provides accurate projection estimation and minimizes artifacts.

The above-described apparatus and manufacturing method, to one skilled in the art, is capable of being adapted for various purposes and is viable for, but not limited to, applications including MRI systems, CT systems, radiotherapy systems, X-ray imaging systems, ultrasound systems, nuclear imaging systems, magnetic resonance spectroscopy systems, and other applications known in the art. The above-described invention can also be varied without deviating from the true scope of the invention.

All documents, patents, journal articles and other materials cited in the present application are hereby incorporated by reference.

Although the present invention has been fully described in conjunction with the preferred embodiment thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. An imaging system comprising:
   a source generating a x-ray beam;
   a detector array receiving said x-ray beam and generating projection data corresponding to at least a scanned portion of an object based on said received x-ray beam; and
   an image reconstructor electrically coupled to said detector array for reconstructing an image of said scanned portion of said object for a full field-of-view in response to said projection data using a dual iterative reconstruction technique comprising:
   reconstructing said full field-of-view using a first resolution; and reconstructing a region-of-interest within said full field-of-view using a second resolution.

2. The system of claim 1, wherein said image reconstructor in reconstructing said image uses a dual iterative reconstruction technique comprising a combined reconstruction technique.

3. The system of claim 2, wherein said combined reconstruction technique comprises:
reconstructing said image for said full field-of-view using filtered backprojection; and
updating a region-of-interest within said full field-of-view using iterative reconstruction.

4. The system of claim 1, wherein said image reconstructor in reconstructing said image uses a dual iterative reconstruction technique comprising a multi-resolution reconstruction technique.

5. The system of claim 4, wherein said multi-resolution reconstruction technique comprises reconstructing an image with a higher spatial resolution for a region-of-interest, within said full field-of-view, than for an area of said full field-of-view outside said region-of-interest.

6. The system of claim 1, wherein said image reconstructor in reconstructing said image uses a dual iterative reconstruction technique comprising a segmentation reconstruction technique.

7. The system of claim 6, wherein said segmentation reconstruction technique comprises:
segmenting said full field-of-view into sub-regions; and
updating each of said sub-regions in response to filtered backprojection data.

8. The system of claim 6, wherein said segmentation reconstruction technique comprises:
determining a frequency with which each pixel in a plurality of pixels associated with said region-of-interest are updated during reconstruction iterations; and
updating each pixel with said frequency.

9. A method of reconstructing an image of an object for an imaging system comprising:
providing projection data corresponding to at least a scanned portion of an object; and
reconstructing an image of said scanned portion of said object for a full field-of-view based on said projection data using a dual iterative reconstruction technique comprising:
reconstructing said full field-of-view using a first resolution; and
reconstructing a region-of-interest within said full field-of-view using a second resolution.

10. The method of claim 9, wherein said projection data is generated based on a received x-ray beam.

11. The method of claim 10, further comprising generating said x-ray beam.

12. The method of claim 9, wherein reconstructing said image comprises performing a dual iterative reconstruction technique comprising a combined reconstruction technique.

13. The method of claim 12, wherein said combined reconstruction techniques comprises:
reconstructing the image for said full field-of-view using filtered backprojection; and
updating a region-of-interest within said full field-of-view using an iterative reconstruction technique.

14. The method of claim 13, wherein said iterative reconstruction is performed using a maximum a-posteriori technique.

15. The method of claim 13, wherein said iterative reconstruction is performed using an expectation-maximization technique.

16. The method of claim 13, wherein said iterative reconstruction is performed using an ordered subsets technique.

17. The method of claim 13, further comprising continuously monitoring progress of said iterative reconstruction technique comprising updating said filtered backprojection image when a convergence measure does not satisfy a pre-determined condition with said iterative reconstruction technique.

18. The method of claim 9, wherein reconstructing said image comprises performing a dual iterative reconstruction technique comprising a multi-resolution reconstruction technique.

19. The method of claim 18, wherein said multi-resolution reconstruction technique comprises: reconstructing an image with a larger spatial resolution for a region-of-interest within said full field-of-view, than for an area of said full field-of-view outside said region-of-interest.

20. The method of claim 18, wherein said multi-resolution reconstruction technique comprises: varying in-plane resolution or image slice thickness between a region-of-interest within said full field-of-view and an area of said full field-of-view outside said region-of-interest.

21. The method of claim 18, wherein said multi-resolution reconstruction technique is applied as a function of iteration.

22. The method of claim 21, wherein applying said multi-resolution reconstruction technique applied as a function of iteration comprises varying number of pixel updates for differing resolutions depending upon interest level criteria associated with each pixel.

23. The method of claim 18, wherein said multi-resolution reconstruction technique comprises reducing the resolution of said projection data for areas of said full field-of-view not within a region-of-interest of said full field-of-view.

24. The method of claim 18, wherein said multi-resolution reconstruction technique comprises separating said weighted projection data into subsets and updating pixels with pre-determined subsets.

25. The method of claim 9, wherein reconstructing said image comprises performing a dual iterative reconstruction technique comprising a segmentation reconstruction technique.

26. The method of claim 25, wherein said segmentation reconstruction technique comprises:
segmenting said full field-of-view into sub-regions; and
updating each of said sub-regions in response to filtered backprojection data.

27. The method of claim 25, wherein said segmentation reconstruction technique comprises:
determining frequency with which each pixel in a plurality of pixels associated with a region-of-interest within said full field-of-view is updated during reconstruction iterations; and
updating each pixel with said frequency.

* * * * *